United States Patent
Falkenhagen et al.

(10) Patent No.: US 9,440,019 B2
(45) Date of Patent: Sep. 13, 2016

(54) SORBENT FOR ENDOTOXINS

(75) Inventors: Dieter Falkenhagen, Krems (AT); Stephan Harm, Krustetten (AT); Jens Hartmann, Furth (AT); Viktoria Weber, Krems (AT)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 558 days.

(21) Appl. No.: 13/806,184

(22) PCT Filed: Jun. 22, 2011

(86) PCT No.: PCT/AT2011/000273
§ 371 (c)(1),
(2), (4) Date: Jan. 15, 2013

(87) PCT Pub. No.: WO2011/160149
PCT Pub. Date: Dec. 29, 2011

(65) Prior Publication Data
US 2013/0105396 A1   May 2, 2013

(30) Foreign Application Priority Data
Jun. 24, 2010   (AT) .................................. 1073/2010

(51) Int. Cl.
| | |
|---|---|
| A61M 1/36 | (2006.01) |
| B01J 20/32 | (2006.01) |
| A61M 1/34 | (2006.01) |
| B01J 20/26 | (2006.01) |
| B01J 20/28 | (2006.01) |

(52) U.S. Cl.
CPC ............ *A61M 1/36* (2013.01); *A61M 1/3472* (2013.01); *A61M 1/3486* (2014.02); *B01J 20/267* (2013.01); *B01J 20/28004* (2013.01); *B01J 20/28078* (2013.01); *B01J 20/321* (2013.01); *B01J 20/3248* (2013.01); *B01J 20/3251* (2013.01); *B01J 20/3253* (2013.01); *B01J 20/3255* (2013.01); *B01J 20/3274* (2013.01); *B01J 20/3285* (2013.01)

(58) Field of Classification Search
None
See application file for complete search history.

(56) References Cited

U.S. PATENT DOCUMENTS

| | | | |
|---|---|---|---|
| 5,177,059 A * | 1/1993 | Handley et al. | ................ 514/2.4 |
| 5,510,242 A * | 4/1996 | Blais et al. | .................. 435/7.32 |
| 5,855,782 A | 1/1999 | Falkenhagen et al. | |
| 6,500,481 B1 * | 12/2002 | Vanderlaan et al. | ......... 427/2.24 |

(Continued)

FOREIGN PATENT DOCUMENTS

WO   2010083545 A2   7/2010

OTHER PUBLICATIONS

International Search Report of International Application No. PCT/AT2011/000273.

*Primary Examiner* — Krishnan S Menon
*Assistant Examiner* — Bradley R Spies
(74) *Attorney, Agent, or Firm* — Sutherland Asbill & Brennan LLP

(57) ABSTRACT

The invention relates to a sorption agent for removing endotoxins from a biological fluid, comprising a water-insoluble, porous carrier having a neutral hydrophobic surface wherein the surface of the carrier has an adsorptive coating made of polymyxin and albumin, wherein polymyxin and albumin are bonded to the surface of the carrier in a noncovalent manner. The invention further relates to a method for producing such a sorption agent. The sorption agent is used in extracorporeal blood purification, in particular in order to treat individuals, who have sepsis.

18 Claims, 2 Drawing Sheets

(56) References Cited

U.S. PATENT DOCUMENTS

Figure 1:
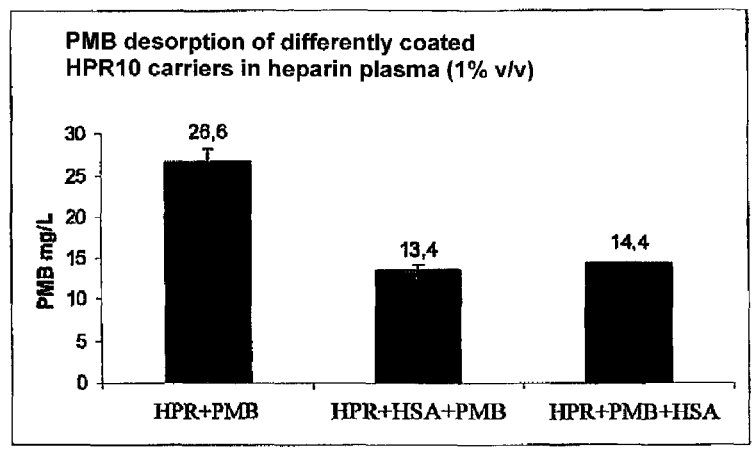

| | | | |
|---|---|---|---|
| 6,531,159 B1* | 3/2003 | Masuko et al. | 424/489 |
| 2001/0055762 A1* | 12/2001 | Suzuki et al. | 435/6 |
| 2004/0110678 A1* | 6/2004 | Siligardi et al. | 514/12 |
| 2004/0202783 A1* | 10/2004 | Baumann et al. | 427/213.3 |
| 2008/0213523 A1* | 9/2008 | Fujimoto et al. | 428/36.5 |
| 2010/0100027 A1* | 4/2010 | Schilthuizen et al. | 604/6.09 |

* cited by examiner

SORBENT FOR ENDOTOXINS

CROSS-REFERERNCE TO RELATED APPLICATIONS

This application is the national stage of International Application No. PCT/AT/2011/00273, filed Jun. 22, 2011, and claim priority benefit of Austrian Patent Application No. A 1073/2010, filed Jun. 24, 2010. These applications are incorporated by reference herein.

The invention relates to a polmyxin coated sorption agent for removing endotoxins from a biological fluid.

Endotoxins are lipopolysaccharides (LPS) in the cell wall of gram-negative bacteria and are released by cell lysis. In fact, lipopolysaccharides are the most frequent lipid component of the external cell membrane of gram-negative bacteria. Endotoxins are pyrogenic substances, i.e. the affected individuum exhibits a strong inflammatory reaction and fever as endotoxins, for example in the course of a microbial intoxification, are reaching into the body and showing their systemic effects. The presence of endotoxins in the blood circuit leads to an uncontrolled activation of immune cells and an imbalance in the coagulation system. Depending on their concentration they may cause a sepsis which is characterized, among others, by a high fever, low blood pressure and, in severe cases, by multiple organ failure. Sepsis is a disease to be taken very seriously; the lethality of individuals having severe sepsis or septic shock amounts to approx. 30-60%, depending on the severity of the disease. Further, patients with a compromised immune defense such as e.g. liver patients or patients in chemotherapy, tend to bacterial infections and thereby show symptoms of an endotoxin intoxification.

The structure of a lipopolysaccharide molecule is tripartite: a lipid A forms the region of the molecule which is turned towards the bacterial cell; it is lipid A that anchors the molecule to the external membrane of the gram-negative bacterium. Further, the LPS molecule has a central, highly conserved core region, which is bound to the lipid A. The third and outermost region is formed by an O-specific polysaccharide (O-antigen), the structure of which may vary strongly within different gram-negative bacteria. The toxic effect can be traced back to lipid A, which is released only at cell lysis.

Endotoxins can be removed from a biological fluid such as blood or plasma, which is contaminated by endotoxins, by an appropriate sorption agent. The treatment of patients who have endotoxin intoxification or sepsis takes place in particular in the course of an extracorporeal blood purification (apheresis).

The processes of apheresis are extracorporeally performed procedures, at which pathophysiologically relevant blood and plasma components, for example biomolecules such as (glyco)proteins, peptides, lipids, lipoproteins and lipopolysaccharides, as well as blood cells and blood plasma, are removed. Apheresis processes may on one hand be employed for diagnostic and therapeutic purposes, and on the other hand they constitute a very effective opportunity of yielding certain blood components of healthy individuals in a sufficient quantity and at a sufficiently high purity. Great significance is attributed to therapeutical apheresis because, at certain indications, it offers a very effective alternative of minimal side effects to medicative treatments. Thus, at plasmapheresis processes, the plasma may either be separated entirely and replaced by a substitution solution, or only certain components such as LDL, endotoxins or immunoglobulins are separated therefrom by way of a sorption agent, following which the plasma is returned to the donor/patient.

In order to remove endotoxins from a biological fluid (in most cases blood or blood plasma), which is contaminated by endotoxins, it is brought into close contact with a sorption agent which is usually contained in a sorption apparatus. The endotoxins get bonded to the surface of the sorption agent and are thus removed from the biological fluid. The biological fluid freed of endotoxins is returned to the patient. This sorption apparatus is either aligned in an extracorporeal blood circuit on the blood side or in a plasma circuit of an extracorporeal blood purification unit on the filtrate side. In this process, the capacity and speed of binding endotoxins is dependent on the nature of this sorption agent.

The speed of the endotoxin binding by the sorption agent is decisive for the survival of the patient. The time left to remove the endotoxins from the patient's blood is very short (<12 h) and may in sepsis be only several hours.

It has been shown that anion exchange resins (e.g. DEAE oder PEI groups bound to cellulose) are very well suited for the binding of endotoxins. However, the undesired binding of important factors of the intracorporeal coagulation system such as protein C and protein S and the coagulation problems connected thereto, are disadvantageous.

These coagulation problems can be avoided by the use of a specific sorption agent which incorporates immobilized antibodies to endotoxins. However, this possibility has only limited applicability for economic reasons.

Sorption agents of the type mentioned at the beginning, in which polymyxin molecules are immobilized on a water-insoluble, porous carrier, have become known as very useful alternatives.

Polymyxins are antibiotic substances for treating infections with gram-negative bacteria. Polymyxins interfere with the cell wall structure by increasing the permeability of the cell membrane which causes a cell to lyse. Polymyxins not only bind phospholipids but rather also lipopolysaccharides (endotoxins) with high affinity. Because of the neurotoxic and nephrotoxic effects of the polymyxins, only polymyxin B and polymyxin E (colistin) have reached a certain therapeutic significance. Polymyxin B and polymyxin E are therefore only applicable for oral and topical treatment forms. They are unsuitable for parenteral, systemic treatment of endotoxin intoxification or sepsis because of their toxic effect.

Due to the neurotoxic and nephrotoxic effects of the polymyxins it is important with respect to patient safety in the clinical application of a polymyxin coated sorption agent to aim for a binding of the polymyxin to the carrier which is as solid as possible in order to keep a polymyxin contamination of the patient's blood, e.g. by polymyxins detaching themselves from the carrier, as low as possible or to prevent it. Therefore, it has seemingly been found necessary to covalently bond polymyxin, in particular polymyxin B, to a water-insoluble carrier and to employ the carrier thus coated with polymyxin B as a sorption agent for the endotoxin removal from contaminated biological fluids.

Polymyxin B-immobilized carriers made of porous glass (FPG 2000) and polymyxin B-immobilized polysaccharide carriers based on cellulose (Cellulofine A-3) are disclosed in EP 0110 409 A. Microparticles made of cellulose or derivatized cellulose, to which polymyxin B is covalently bonded, are also known [Weber V., Loth F., Linsberger I., Falkenhagen D.: Int. J. Artif. Organs 25(7), 679]. A high level of endotoxin adsorption could be achieved using polymyxin-coated cellulose carriers, however, they have the disadvantage that polymyxin B has to be covalently bonded to these carriers with considerable effort and that the cellulose must therefore be chemically activated prior to the binding of the polymyxin.

EP 0 129 786 A2 describes an endotoxin detoxification material having a fibrous carrier, on which polymyxin is covalently immobilized. The fibrous carrier is provided with functional groups to covalently bond polymyxin to the surface of the carrier. The endotoxin detoxification material from EP 0 129 786 is on the market as a filler material for an adsorption module (trade name: Toraymyxin) [Shoji H. 2003. Extracorporeal endotoxin removal for the treatment of sepsis: endotoxin adsorption cartridge (Toraymyxin)] and at the moment is the only sorption agent which is approved for commercial use in the clinical treatment of sepsis for eliminating endotoxins in the scope of extracorporeal blood purification. A critical review of the effectiveness of fibrous carriers having immobilized polymyxin B, in which the quality of the treatment is represented as suboptimal, has been published [Cruz DN et al. 2007; Effectiveness of polymyxin B-immobilized fiber column in sepsis: a systematic review. Crit. Care 11(3): 137].

The known sorption agents which are based on binding of the endotoxins by polymyxin have the disadvantage of low endotoxin binding capacity and speed. Since polymyxin is bound to the polymer via $NH_2$ groups, the access for endotoxins is impaired. Further disadvantages result from the costly and complex production method and the higher production costs connected thereto.

Although the lethality of patients having endotoxin intoxification, in particular sepsis, has been able to be reduced by the clinical administration of the above mentioned Toraymyxin adsorption module, the lethality of patients having severe sepsis and septic shock is still very high in spite of maximum therapy. For this reason and because of the high and rising incidence of septic states, there is a high demand for a sorption agent having improved sorption performance for endotoxins and which, moreover, complies with the high safety requirements with respect to its clinical administration.

It is an object of the invention to provide a sorption agent, using which endotoxins can be removed to a high degree and at high speed from a biological fluid and which, moreover, does not constitute an additional health risk to the patient but is safe in the clinical application.

The object is achieved by a polymyxin-coated sorption agent for removing endotoxins from a biological fluid as mentioned at the beginning, which according to the invention comprises of water-insoluble, porous carrier having a neutral hydrophobic surface wherein the surface of the carrier has an adsorption agent coating made of polymyxin and albumin, wherein polymyxin and albumin are bonded to the surface of the carrier in a noncovalent manner.

Thanks to the sorption agent according to the invention, a significant improvement of the endotoxin sorption capacity and endotoxin sorption speed has been able to be achieved, compared to sorption agents, in which polymyxin is bonded covalently. The inventors have established to an unexpected extent that—in comparison to the known sorption agents—a large endotoxin quantity can already be bound from an endotoxin contaminated biological fluid after a short action time by the sorption agent according to the invention. This is great therapeutic advantages, in particular for patients having sepsis since a large volume of biological fluid can be freed of endotoxins in a short time. The survival chances of patients having severe sepsis can be improved by the sorption agent according to the invention. As already mentioned, the speed of the endotoxin binding by the sorption agent is decisive for the survival of the patient. The treatment duration in the scope of extracorporeal blood purification can also be shortened thanks to the sorption agent according to the invention, whereby chronological, financial and human resources can be saved.

Moreover, the inventors noted the surprising fact that a desorption of the polymyxin from the surface of the carrier can significantly be reduced thanks to the adsorption agent coating of the carrier with both, polymyxin and albumin, compared to a carrier, which is adsorptively coated with polymyxin only. Thanks to the invention, significantly less polymyxin is desorbed from the carrier surface. Consequently, significantly less toxic polymyxin gets into the biological fluid, in particular into the blood, whereby the safety for the patient may be maintained at a very high level. The additional coating with albumin did not impair endotoxin sorption by the polymyxin, compared to a carrier which was adsorptively coated with polymyxin only.

As already mentioned, many absorbers have the disadvantage of eliminating not only the substances to be removed but also physiologically important proteins and/or factors of the blood coagulation system (both anticoagulants and procoagulants) at a very high level. Further, it could be established that important natural coagulation factors of the blood such as protein C or coagulation inhibitors which were added to the blood such as heparin are adsorbed to an insignificant degree by the sorption agent according to the invention, and surprisingly, a lower adsorption of heparin and protein C by the sorption agent of the invention was even observed, compared to a carrier coated with polymyxin only. The risk of an imbalance of the introcorporeal coagulation system or an undesired anticoagulation in the extracorporeal or intracorporeal blood circuit can thus be minimized.

A further advantage of the invention in relation to the known sorption agents is its particularly simple production. Compared to the sorption agents known from the state of the art, polymyxin is not bonded covalently, but is immobilized—using the hydrophobic section of the polymyxin molecule—in particular via hydrophobic interaction on the neutral, hydrophobic surface of the carrier. The increase in the endotoxin binding effectiveness of the sorption agent according to the invention may be explained in that the binding mediated using hydrophobic interaction leaves the $NH_2$ groups of the polymyxin exposed and these are available essentially in their entirety for the endotoxin binding. No complex chemical steps are required for immobilizing the polymyxin on the carrier. Neither does the albumin binding occur covalently, but also via adsorptive processes, which neither requires any additional chemical immobilizing and crosslinking steps or the use of chemicals, which had to be removed without any residues prior to the clinical application of the sorption agent. Adsorptively coating surfaces with albumins constitutes a known method; in immunoassays for example, e.g. ELISA, bovine serum albumin (BSA) is employed to prevent an unspecific binding. The production of the sorption agent according to the invention can therefore be performed economically, reproducibly and without using any additional chemicals.

The term "adsorptive coating" of polymyxin and albumin therefore means that polymyxin and albumin bind to the surface via adsorptive processes and are thus noncovalently bonded to the surface of the carrier. As already mentioned above, it can be assumed that hydrophobic interaction in particular is playing an important role. Hydrophobic interaction is of large biochemical significance and is based on the phenomenon that hydrophobic molecules tend to associate in a polar environment. Hydrophobic interaction is thus no force by itself but is forced by a polar environment. In the present invention, hydrophobic interaction occurs in particular between the hydrophobic section of the polymyxin molecule and the hydrophobic side chains of the albumin and the neutral, hydrophobic internal and external surfaces of the porous carrier. A person of skill in the art is familiar with the adsorptive coating of surfaces with amphiphilic molecules. For example, some principal chromatographic separation methods such as, for example, HIC (hydrophobic interaction chromatography) or the reversed phase chromatography are based on the principle of hydrophobic interaction, which ususally achieves a very solid binding of the molecules to the carrier surface. Other noncovalent interactions, including, without restriction, ionic binding, hydrogen bridge binding and van der Waal interactions, may play a role in the adsorption of polymyxin and albumin, too. One possible explanation of the effect according to the invention is the fact that the desorption of polymyxin by a plurality of noncovalent interactions between the polymyxin and albumin molecules is reduced, which achieves the effect according to the invention.

The term "sorption agent" in the context of this disclosure is to be understood as an agent for performing a sorption, preferably an adsorption, i.e. molecules which are located in a biological fluid are fixed by the surface forces of the sorption agent. In the description, the terms "adsorption agent" or "adsorption agent" or "adsorber" are also used instead of the term "sorption agent". According to the invention, the sorption agent is provided for the adsorption of endotoxins from a biological fluid contaminated with endotoxins. The sorption agent according to the invention is used above all in extracorporeal blood purification, in particular in patients having septic states.

The term "albumin", as used herein, refers to naturally occurring albumin, in particular human albumin, analogues and variants thereof. Further, the term "albumin" comprises albumin-like polypetides. Albumin-like polypeptides are similar to albumin with respect to their structure and have albumin-like properties. Albumin-like polypeptides are derived among others from subtypes of albumins such as, for example, prealbumins. Albumin-like polypeptides may either be from natural sources or may be produced synthetically.

The expression "biological fluid" used in the scope of the invention can relate to cell-free liquids, in particular blood plasma, and to liquids containing cells, in particular blood. Since it is also necessary in the course of extracorporeal blood purification to introduce other liquids, for example, solutions containing coagulation inhibitors (heparin solution, citrate solution) or substitution solutions (electrolytes, liquids to compensate for the liquid loss) into the extracorporeal blood circuit or into a blood plasma circuit, a biological fluid is also to be understood as diluted blood or diluted blood plasma. The invention is primarily intended for the field of human medicine and therefore primarily relates to human biological fluids. However, this does not preclude the invention also being used in the veterinary field.

Polymyxins are known chemical compounds which originally originate from the bacteria *Bacillus polymyxa*. Polymyxin B and polymyxin E (colistin) are noted in particular as being useful in the invention.

The term "water-insoluble, porous carrier, which has a neutral, hydrophobic surface" as used in independent claim 1 relates in the context of this disclosure to a porous, water-insoluble solid, which has external and internal surfaces. The external and internal surfaces are neutral and hydrophobic. The term "neutral" is to be understood as non-ionic. The invention is directed above all to particulate carriers.

In the production of a sorption agent according to the invention, polymyxin and albumin are adsorbed to the carrier in separate, sequential coating steps. Thereby, it has proven useful to first adsorptively coat the carrier with polymyxin and, following a washing step to remove any excess polymyxins, to subsequently carry out adsorptive coating with albumin. This makes it possible to introduce an autoclaving step between the two coating steps. In principle, it is also possible to first coat the carrier with albumin and subsequently with polymyxin; however, the sterile production of such carriers is more cumbersome because the albumin coating denaturizes under the autoclaving conditions and consequently all steps have to be carried out with sterile, in particular sterile filtered solutions. It is therefore advantageous to sterilize the carrier after having adsorptively coated it with polymyxin and to subsequently perform the coating with albumin. Sterile albumin solutions which are also suitable for the production of the sorption agent according to the invention are employed frequently and are commercially available (e.g. Human Albumin, 20%, Octapharma, Vienna, Austria).

A sorption agent according to the invention is preferably produced by a method, which also constitutes part of the invention, which is comprised of the following steps:

a) Providing a water-insoluble, porous carrier which has a neutral, hydrophobic surface, b) adsorptively coating the surface of the carrier with polymyxin by contacting and incubating the carrier with an aqueous, polymyxin-containing solution, c) washing the carrier to remove any unbound polymyxin, d) adsorptively coating the polymyxin-coated surface of the carrier with albumin by contacting and incubating the carrier with an aqueous, albumin-containing solution, and e) as appropriate, washing the carrier to remove any unbound albumin.

The washing step e) is optional and may thus be omitted. Is the carrier coated with polymyxin and albumin to be temporarily stored for a longer period prior to its application, however, it is appropriate to carry out step e) prior to its storage.

Pharmaceutically acceptable salts are used for the preparation of the aqueous solutions containing polymyxin and albumin. Pharmaceutically acceptable cations such as sodium are used in order to influence the ion strength. With respect to the application for blood purification, whereby the sorption agent comes into direct contact with the blood, albumin is preferably diluted in an isotonic solution, more preferably in isotonic saline. As mentioned above, suitable sterile albumin solutions are commercially available. In the production process, washing the carrier to remove any unbound polymyxin or albumin is preferably also done with an isotonic solution, in particular isotonic saline.

In order to satisfy to the high requirements with respect to the sterility of the sorption agent it is useful to autoclave the carrier between the steps b) and c) or between the steps c) and d). Autoclaving is done in accordance with established practice, for example at 121° C. for 20 min. It will be understood by a skilled person that the solutions to be used after autoclaving, i.e. the aqueous, albumin-containing solution and the solution employed for washing, should conform to clinical requirements, i.e. they especially have to be sterile and pyrogen-free.

It is particularly expedient in practice if the carrier is a hydrophobic polymer. Good reproducibility of the carrier material can thus be ensured, in particular with respect to the porosity and the particle size. The porosity and the particle size may additionally be varied very well. The hydrophobic polymer can be both a homopolymer and also a heteropolymer. Cross-linked polystyrene polymers have proven to be particularly favorable for practical performance. During extracorporeal blood purification, there are high requirements concerning the sterility of the device components which come into contact with the bodily fluids of a patient. This also applies to sorption agents. Cross-linked polystyrene polymers are distinguished by high stability with respect to heat and chemicals and are already established in clinical practice.

The strength of the hydrophobic interaction between polymyxin and carrier is determined, on the one hand, by the hydrophobicity of the neutral, hydrophobic carrier and, on the other side, by the ionic strength of the medium. As already mentioned above, polymyxin has neurotoxic and nephrotoxic effects. Therefore, the most possible solid binding of the polymyxin to the external and internal surfaces of the carrier is desired. In a particularly preferred variant, the cross-linked polystyrene polymer is a polystyrene-divinyl benzene copolymer. The surface of a polystyrene-divinyl benzene copolymer has a high hydrophobicity whereby very strong binding of the polymyxin to the carrier surface is achieved. It is of course possible to use other neutral, hydrophobic polymers of a high hydrophobicity which are well-known to a person skilled in the art. However, it has been found that after immobilizing the polymyxin on a neutral, hydrophobic polymer, still certain amounts of polymyxin are desorbing from the carrier surface and are released into the biological fluid. Indeed, this desorption does not significantly affect the endotoxin sorption capacity of the polymyxin; however, even small amounts of polymyxin may show neurotoxic and nephrotoxic effects and may therefore constitute a health risk to the patient. The desorption of the polymyxin can be significantly reduced thanks to the sorption agent according to the invention which is additionally coated with albumin besides the polymyxin.

Furthermore, it has been found that the pore size of the porous carrier is also significant with respect to the endotoxin adsorption. It is therefore favorable, also for reasons of reproducibility, if the porous carrier has a defined mean pore size. The mean pore size of the carrier always relates to that before the immobilization of the polymyxin via hydrophobic interaction.

The mean pore size can be set particularly well if the porous carrier is produced from a synthetic polymer. Although a person skilled in the art in this field what the term "mean pore size" is to be understood as and how the porosity or the mean pore size can be intentionally set, this term will nonetheless be briefly defined for reasons of clarity. The mean pore size relates to the mean diameter of the pores. In a Gaussian size distribution of the pore diameters of a porous material, the mean pore diameter is the pore diameter which corresponds to the maximum of the distribution curve. The mean pore diameter can be determined using nitrogen adsorption (as described in Weber et al. 2008; Neutral styrene-divinyl benzene copolymers for adsorption of toxins in liver failure. Biomacromolecules 9(4): 1322-1328) or using mercury intrusion, for example. The pore size of a polymer is set by variation of the concentration of the participating monomers or co-monomers, the solvent, or the modulator. The smaller the pores of the polymer are selected to be, the larger the internal surface area of the polymer which is available for sorption, in particular adsorption. The larger the pores, the better the accessibility of the pores for larger molecules. A production method for a synthetic, hydrophobic polymer of a defined pore size, as can be used for the invention, is described in the above mentioned publication by Weber et al.

It has been shown that particularly good endotoxin sorption can be achieved by the sorption agent if the carrier has a mean pore size of at least 15 nm. The carrier preferably has a mean pore size of at least 30 nm. For clinical application of extracorporeal blood purification, however, it is favorable if the mean pore size of the uncoated carrier is not greater than 120 nm. The internal surface area of the sorption agent would otherwise become to small; the result would be a reduction of the endotoxin sorption capacity (endotoxin adsorption capacity). Preferably, the carrier therefore has a mean pore size chosen out of the range of 15 nm to 120 nm.

In a variant, the uncoated carrier has advantageously a mean pore size of about 30-40 nm. In this variation, the elimination of endotoxins from a biological fluid occurs with particularly high speed and high efficiency. Only a small amount of sorption agent is therefore required to bind a large quantity of endotoxin.

For example, the concentration of the sorption agent according to the invention, when it is used as a suspension in an extracorporeal plasma circuit, can be selected as 1% (Vol %). An extracorporeal plasma circuit which contains a suspension of a sorption agent in the form of microparticles represents a central component of a Microspheres-based Detoxification System (MDS). An MDS is known from EP 0776223 B and U.S. Pat. No. 5,855,782.

In addition, the form of the sorption agent according to the invention during the sorption procedure is also significant. In an advantageous variant, the sorption agent according to the invention is in the form of microparticles. The particle size influences the kinetics of the adsorption. In addition, with a small particle size, there is a large surface area/volume ratio. In an advantageous subvariant, the microparticles have a particle size of 20 μm or less.

The microparticles are used in particular in an MDS, which was already mentioned above. The microparticles circulate as a suspension in a purification circuit (plasma circuit) on the filtrate side of a membrane filter. However, if the membrane filter leaks, the danger exists that microparticles will reach the extracorporeal blood circuit and then the body of the patient and will result in a lung embolism therein. For this reason, it is advantageous in a further subvariant if the microparticles have a particle size of 8 μm or less, ideally 5 μm or less, since the danger of a lung embolism can be avoided at these small particle sizes.

The sorption agent according to the invention is primarily provided for use in extracorporeal blood purification (apheresis).

In an important application of the invention, the sorption agent can be used as a filler material for a sorption apparatus. The sorption apparatus can be implemented as a column or cartridge. Depending on which blood purification device or which blood purification method (hemoperfusion, plasmapheresis/plasmasorption) is used, the sorption apparatus can be situated on the blood side in an extracorporeal blood circuit or in a plasma circuit on the filtrate side. The biological fluid (blood or blood plasma) passes the sorption apparatus, the endotoxins binding to the immobilized polymyxin molecules of the sorption agent. The purified blood or plasma is returned to the patient.

A further possible use relates to a plasma circuit, in which the sorption agent is provided distributed as a suspension in the plasma. An example of such a plasma circuit is found as a device element in an above described MDS. The sorption agent provided in suspension in a plasma circuit is preferably in the form of microparticles.

Although the endotoxin sorption agent according to the invention is primarily provided for use in extracorporeal blood purification (apheresis), usage in chromatography is also conceivable. The sorption agent can thus be used as a filler material in chromatography columns for purifying endotoxin-contaminated blood or blood plasma. Other applications for removing endotoxins from biological fluids or water are also conceivable.

The sorption agent according to the invention or a sorption apparatus containing a sorption agent according to the invention or a plasma circuit containing a suspension of a sorption agent according to the invention is particularly suitable for treating a sepsis.

Furthermore, the invention relates to a method for removing endotoxins from a biological fluid, in which a biological fluid contaminated with endotoxins is brought into contact with the sorption agent according to the invention. As described above, the biological fluid can pass a sorption apparatus which contains the sorption agent. However, the sorption agent can also be suspended in the biological fluid. An example of the latter is the above described MDS. The biological fluid can be blood or blood plasma.

The present invention is explained in greater detail hereafter on the basis of non-restrictive examples.

1. Example 1: Production of Sorption Agents (Adsorbers) According to the Invention To produce sorption agents according to the invention, neutral, hydrophobic polystyrene-divinyl benzene copolymers were adsorptively coated first with polymyxin B (PMB) and then with human serum albumin (HSA).

1.1. Providing a Water-Insoluble, Porous Carrier Having a Neutral, Hydrophobic Surface Polystyrene-divinyl benzene copolymers of varying particle sizes (in the following, briefly referred to as "polymer" or "carrier" or "uncoated adsorber") were purchased from Dow Chemical Comp. and had a mean pore size of 30 to 40 nm. The polystyrene-divinyl benzene copolymers are listed in table 1.

TABLE 1

Polystyrene-divinyl benzene copolymers

| Designation | Designation by the manufacturer | Particle size [μm] |
|---|---|---|
| #1824 | Microadsorber | 5 |
| HPR10 | Amberchrom ® HPR10 | 10 |

Carrier #1824 was supplied by the manufacturer in suspension and washed 5 x in NaCl.
Carrier HPR10 ist pretreated according to the instructions of the manufacturer.

1.2. Adsorptively Coating the Polymers with Polymyxin B (PMB) and Human Serum Albumin (HSA)

The carriers #1824 and HPR10 listed in table 1 were coated with PMB and HSA according to the following steps:

a) For the coating, an adequate amount of PMB solution having a concentration of 5 mg/ml is produced. Polymyxin B (PMB) was purchased from Sigma Comp. (Cat. No.: 81334, batch 1348744). For the oceating, a polymyxin B solution (PMB solution) was produced, 50 mg PMB being dissolved in 10 ml LAL water.

b) The pretreated carrier is centrifuged (4,000 g, 10 min), the supernatant is discarded, and 5 ml of a PMB solution per ml carrier sediment are pipetted into this for the coating.

c) The carrier is incubated with the PMB solution for 60 min at 20° C.

d) Following the incubation period, the adsorber suspension now coated with PMB is autoclaved in sterile glass vials at 121° C. for 20 min.

e) Subsequently, the adsorber coated with PMB is centrifuged (4,000 g, 10 min) and is washed 3 times in 5 volumes of 0.9% NaCl.

f) The adsorber coated with PMB can be put in interim storage into a fridge as a 50% suspension in 0.9% NaCl and can immediately be further coated with HSA.

g) For the adsorptive coating with HSA, an adequate amount of 10% human serum albumin solution (HSA solution) is prepared (source: Human Albumin, 20%, Octapharma, Vienna, Austria).

h) The PMB coated and autoclaved adsorber is centrifuged (4,000 g, 10 min), the supernatant is discarded, and 2.5 ml HSA solution per ml adsorber sediment are pipetted into this for the coating.

i) The adsorber suspension is incubated with the HSA solution for at least 12 h at 10° C.

j) Following the incubation period, the PMB and HSA coated adsorber is washed once in 5 volumes of 0.9% NaCl solution.

k) The PMB and HSA coated adsorber is stored in the fridge as a 50% suspension in 0.9% NaCl.

Since the amount of PMB added for coating the carrier is adsorbed almost entirely, the quantity of PMB amounts to 25 mg per g damp adsorber.

The resulting PMB and HSA coated adsorber according to the invention are summarized in table 2:

TABLE 2

PMB and HSA coated adsorber according to the invention
Designation of the PMB and HSA coated adsorbers

| #1824 + PMB + HAS |
| HPR10 + PMB + HAS |

2. Example 2: Desorption of Polymyxin B and Endotoxin Adsorption—Batch Test 2.1. Adsorber Material The desorption of polymyxin B from the surface of the adsorber HPR10+PMB+HSA and the endotoxin adsorption by the adsorber HPR10+PMB+HSA were examined in a batch test.

The PMB and HSA coated adsorber HPR10+PMB+HSA (production see example 1 in section 1.2) was compared to two additional adsorbers in the polymyxin B desorption test:

HPR10+PMB: Carrier HPR10, coated with PMB only. The production was according to steps a)-f) of the production protocol in section 1.2.

HPR10+HSA+PMB: Carrier HPR10, which was first coated with albumin and then with polymyxin B. The prodcution of this adsorber, which also is an adsorber according to the invention, is carried out according to the following steps a) to j):

a) The pretreated HPR10 carrier is autoclaved as a 50% suspension in 0.9% NaCl at 121° C. for 20 min.

b) Following the autoclaving step, the carrier is centrifuged, after which the coating step with albumin is performed.

c) For the coating, an adequate amount of 10% HSA solution (source: Human Albumin, 20%, Octapharma, Vienna, Austria) is prepared, and 2.5 ml HSA solution per ml carrier sediment are pipetted into this for the coating.
d) The carrier suspension is incubated with the HSA solution for at least 12 h at 10° C.
e) Following the incubation period, the HSA coated HPR10 adsorber is washed once with 5 volumes of 0.9% NaCl solution and is centrifuged (4,000 g, 10 min). The supernatant is discarded and subsequently the coating with PMB is performed:
f) For the PMB coating, an adequate amount of PMB solution is prepared at a concentration of 5 mg/ml. Polymyxin B (PMB) was purchased from Sigma Comp. (Cat. No.: 81334, batch 1348744).
g) 5 ml PMB solution per ml adsorber sediment are pipetted into this for the coating.
h) The adsorber suspension is incubated with the PMB solution at 20° C. for 60 min.
i) Following the incubation period, the adsorber suspension is centrifuged (4,000 g, 10 min) and is washed 3 times with 5 volumes of 0.9% NaCl.
j) The final HPR10 adsorber coated with HSA and PMB (HPR10+HSA+PMB) is stored in a fridge as a 50% suspension in 0.9% NaCl.

HPR10+PMB+HSA and HPR10+PMB were compared to each other in examining the endotoxin adsorption. As a control, a test tube without adsorber (Ko o Ads) was carried along.

2.2. Batch Test

1% (v/v) adsorber (HPR10+PMB, HPR10+HSA+PMB and HPR10+PMB+HSA) were incubated in heparin plasma using an endotoxin spike (5 ng/ml).

LPS *Pseudomonas aeruginosa* (Sigma Comp., L7018, batch 128K4115) was used as the endotoxin spike. The portioned (each 100 µl $10^{-3}$ g/ml (1 mg/ml)) endotoxins, which were stored at −70° C. in microfuge tubes, were thawed and admixed with 900 µl LAL water. Following this, the endotoxins were diluted further in NaCl to the required concentration of 50 ng/ml. In the batch of test, a further dilution of the endotoxin solution was performed to a final concentration of 5 ng/ml.

Samples were taken after 3, 6 and 24 hours and the desorbed quantity of PMB in heparin plasma was analyzed by an PMB assay [Cao et al., 2008. Development and validation of reversed-phase high-performance liquid chromatography assay for polymyxin B in human plasma. Journal of Antimicrobial Chemotherapy 62: 1009-1014]. The batch test was performed with two repeats. The mean PMB desorption after 24 h was 26.6 mg/l with HPR10+PMB, 13.4 mg/l with HPR10+HSA+PMB, and 14.4 mg/l with HPR10+PMB+HSA (see FIG. 1). The desorption of PMB from the surface of the adsorber can be reduced by 45% with the PMB and HSA coated sorption agent according to the invention (HPR+HSA+PMB and HPR+PMB+HSA), compared to a sorption agent, which is coated with polymyxin only (HPR10+PMB).

Figure 2:
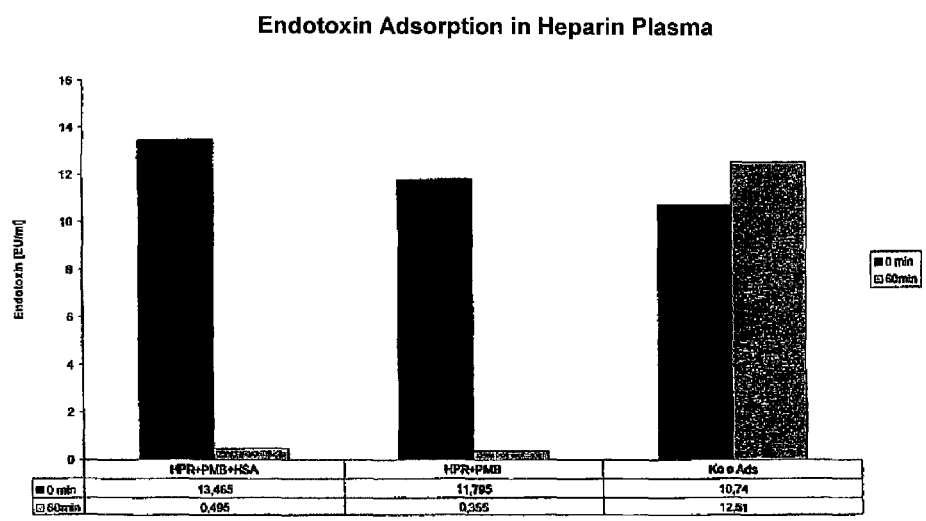

The endotoxin adsorption capacity is not impaired by the additional coating with albumin (see FIG. 2).

In summary, the sorption agent according to the invention does have an equally high endotoxin sorption efficiency and speed like a sorption agent which is coated with polymyxin only. The additional coating with albumin, however, results in a significantly reduced desorption of toxic polymyxin B from the carrier and therefore enhances the safety for the patient.

3. Example 3: Adsorption of Heparin and Protein C 3.1. Background of the Test

Many adsorbers are disadvantageous in that they not only eliminate the substances to be removed, in this case endotoxins, but also physiologically important proteins and factors of the blood coagulation system (both anticoagulants and procoagulants) to a very high level. In this respect, the patient's own coagulation inhibitors such as protein C and protein S must be mentioned in particular. Of particular importance is protein C as being a coagulation inhibiting factor. A reduction of the intracorporeal protein C concentration leads to severe coagulation complications such as vein thrombosis and lung embolism. The anticoagulant heparin, which is additively introduced into the extracorporeal blood circuit by infusion, is eliminated by many adsorbers. This results in an imbalance of the intracorporeal coagulation system and an undesired anticoagulation in the extracorporeal and/or intracorporeal blood circuit, which poses a great hazard to the patient.

Therefore, the tests in this example 3 served to examine the novel sorption agent according to the invention with respect to an undesired adsorption of heparin and protein C. Two different carriers of varying particle sizes (#1824/5 µm and HPR10/10 µm—see example 1) with different coatings (uncoated/coated with polymyxin B only/coated with polymyxin B and human serum albumin) were compared. The adsorption of heparin was examined in heparin plasma (blood plasma admixed with heparin). The adsorption of protein C was examined in citrate plasma (blood plasma admixed with citrate).

3.2. Adsorber Material

Adsorbers with different coatings were compared to each other:
uncoated carrier (#1824 and HPR10),
carrier coated with polymyxin B only (#1824+PMB and HPR10+PMB), and
carrier according to the invention, coated with polymyxin B and albumin (#1824+PMB+HSA and HPR10+PMB+HSA).

50% adsorber suspensions of the adsorbers #1824+PMB+HSA and HPR10+PMB+HSA according to the invention were prepared as described above in the production protocol in section 1.2. The preparation of 50% adsorber suspensions of the adsorbers, which were coated with polymyxin B only, was done according to steps a)-f) of the production protocol in example 1.

The adsorbers used in this example 3 are listed in table 3.

TABLE 3

| Designation of the adsorber | Description of the adsorber |
| --- | --- |
| #1824 | Uncoated microadsorber |
| #1824 + PMB | Microadsorber, coated with polymyxin B |
| #1824 + PMB + HSA | Microadsorber, coated with polymyxin B first and then with HSA |
| HPR10 | Uncoated Amberchrom ® HPR10 |
| HPR10 + PMB | Amberchrom ® HPR10, coated with polymyxin B |
| HPR10 + PMB + HSA | Amberchrom ® HPR10, coated with polymyxin B first and then with HSA |

As a control, a test tube filled with plasma without adsorber (Ko o Ads) was carried along.

3.3. Blood Plasma a) HEPARIN plasma (nominal: 10 IU heparin per ml plasma)
b) CITRATE plasma (nominal: 11 mmol citrate per ml plasma)

3.4. Batch Tests

Two batch tests A and B were carried out. For the batches of the test, 50% adsorber suspensions of the different adsorbers were incubated in test tubes with heparin plasma (batch test A) and with citrate plasma (batch test B), whereby 1470 ml plasma were admixed with 30 ml adsorber suspension in each case.

The adsorption of heparin (in heparin plasma) and protein C (in citrate plasma) was analyzed with time at 0, 15 and 60 minutes:

Sampling after 15 and 60 Minutes:

After 15 min, a sample of 500 µl is removed and centrifuged at 4,000 g, 5 min, and aliquoted: 1×100 µl (protein C), 1×250 µl (heparin), 1×remainder (approx. 150 µl). The aliquots are stored at −20° C. until being analyzed.

After 60 min, a sample of 500 µl is removed and centrifuged at 4,000 g, 5 min, and aliquoted: 1×100 µl (protein C), 1×250 µl (heparin), 1×remainder (approx. 150 µl). The aliquots are stored at −20° C. until being analyzed.

3.5. Results of the Batch Tests

Figure 3:
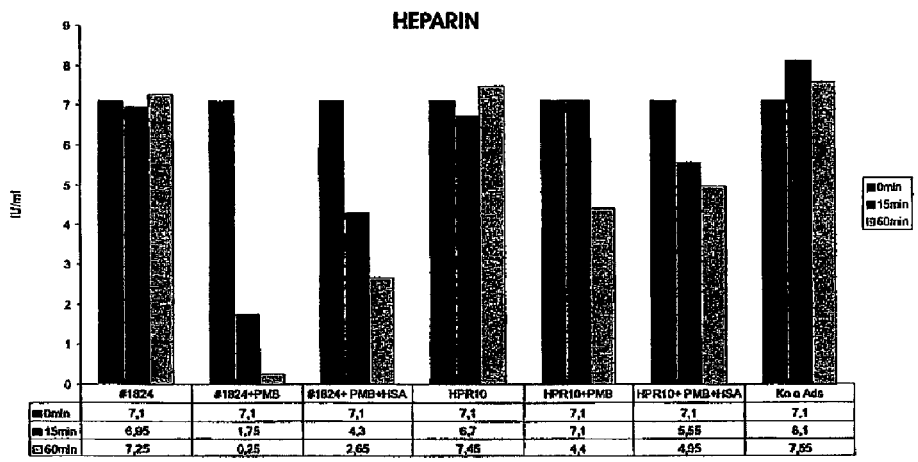
Figure 4:
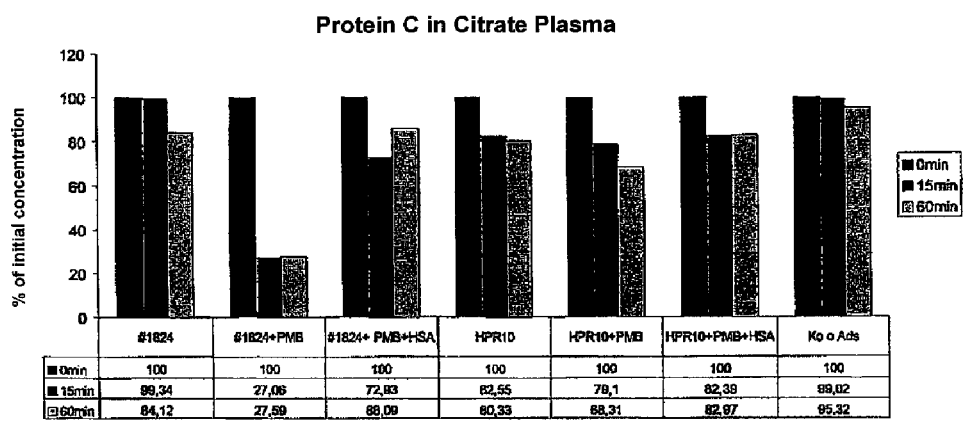

The results of the batch tests are set out in FIGS. 3 and 4:

FIG. 3 shows the adsorption of heparin by the various adsorbers in heparin plasma. Surprisingly, it has been shown that the undesirable adsorption of the heparin can be reduced by using the polymyxin B and HSA coated sorption agent (adsorber) according to the invention—in particular by using the adsorber of a small particle size (5 µm particle size).

FIG. 4 shows the adsorption of protein C by the various adsorbers in citrate plasma. It has been shown that protein C is hardly adsorbed by the adsorbers according to the invention and that the adsorption of protein C, compared to the other adsorbers (uncoated or coated with polymyxin B only), essentially remained the same (HPR10+PMB+HSA–10 µm particle diameter) or was even markedly reduced (#1824+PMB+HSA–5 µm particle diameter).

The invention claimed is:

1. A sorption agent for removing endotoxins from blood or blood plasma, comprising:
   a water-insoluble, porous carrier having a neutral hydrophobic surface wherein the surface of the carrier has an adsorptive coating made of polymyxin B and human serum albumin, wherein the polymyxin B and human serum albumin are noncovalently attached to the surface of the carrier by a hydrophobic interaction.

2. The sorption agent according to claim 1, wherein the carrier is a hydrophobic polymer.

3. The sorption agent according to claim 2, wherein the hydrophobic polymer is a cross-linked polystyrene polymer.

4. The sorption agent according to claim 1, wherein the carrier has a mean pore size of at least 15 nm.

5. The sorption agent according to claim 1, wherein the carrier has a mean pore size of not greater than 120 nm.

6. The sorption agent according to claim 1, wherein the sorption agent has the form of microparticles.

7. The sorption agent according to claim 6, wherein the microparticles have a particle size of 20 µm or less.

8. A sorption apparatus, containing the sorption agent according to claim 1.

9. A plasma circuit, containing a suspension of the sorption agent according to claim 1.

10. A method of producing a sorption agent according to claim 1, comprising the steps of:
   a) providing a water-insoluble, porous carrier which has a neutral, hydrophobic surface,
   b) adsorptively coating the surface of the carrier with polymyxin B by contacting and incubating the carrier with an aqueous, polymyxin B-containing solution,
   c) washing the carrier to remove any unbound polymyxin B,
   d) adsorptively coating the polymyxin B-coated surface of the carrier with human serum albumin by contacting and incubating the carrier with an aqueous, human serum albumin-containing solution, and
   e) as appropriate, washing the carrier to remove any unbound human serum albumin.

11. The method according to claim 10, wherein the carrier is autoclaved between the steps b) and c) or between the steps c) and d).

12. A method for removing endotoxins from blood or blood plasma, comprising:
   bringing blood or blood plasma contaminated with endotoxins into contact with the sorption agent according to claim 1.

13. The method according to claim 12, carried out for the treatment of a sepsis.

14. The method according to claim 12, wherein the sorption agent is included in a Microspheres-based Detoxification System (MDS).

15. The sorption agent according to claim 3, wherein the hydrophobic polymer is a polystyrene-divinyl benzene copolymer.

16. The sorption agent according to claim 4, wherein the carrier has a mean pore size of at least 30 nm.

17. The sorption agent according to claim 7, wherein the microparticles have a particle size of 8 µm or less.

18. The sorption agent according to claim 7, wherein the microparticles have a particle size of 5 µm or less.

* * * * *